United States Patent [19]

Borer et al.

[11] Patent Number: 5,684,007
[45] Date of Patent: Nov. 4, 1997

[54] METHODS FOR INHIBITING CARDIAC FIBROBLAST GROWTH AND CARDIAC FIBROSIS

[75] Inventors: Jeffrey S. Borer, New York; Steven M. Goldfine, Jamaica, both of N.Y.

[73] Assignee: Otsuka Pharmaceutical Co., Ltd., Osaka, Japan

[21] Appl. No.: 708,581

[22] Filed: Sep. 5, 1996

[51] Int. Cl.⁶ .................................................. A61K 31/495
[52] U.S. Cl. .................................................. 514/255
[58] Field of Search .................................................. 514/255

[56] References Cited

U.S. PATENT DOCUMENTS 4,415,572  11/1983  Tominaga et al. ..................... 544/360

OTHER PUBLICATIONS

Borer et al, "Regurgitant Valvular Diseases as a Cause of Heart Failure and Sudden Death: Cell Biology an Pathophysiology", *J. of Heart Failure*, 3(1):84 (Abstract 333) (May 1996).

Yoshinaka et al, "Alterations of the Cytoskeletal Organization in Tumor Cell Lines by a Cardiotonic Drug, Vesnarinone, through Protein Tyrosine Phosphorylation", *Experimental Cell Research*, 219:21–28 (1995).

Ross et al, "Low Dose, But Not High Dose, Vesnarinone Decreases Survival of Cardiac Fibroblasts Isolated from Normal and Aoric Regurgitant Hearts", *J. of Investigative Medicine*, 44(7):408A (Sep. 1996).

*Primary Examiner*—Raymond Henley, III
*Attorney, Agent, or Firm*—Sughrue, Mion, Zinn, Macpeak & Seas, PLLC

[57] ABSTRACT

Methods are disclosed for inhibiting cardiac fibroblast growth, and for inhibiting cardiac fibrosis, wherein said methods use, as the active agent, a carbostyril derivative.

5 Claims, 2 Drawing Sheets

CARDIAC FIBROBLAST GROWTH CURVES
WITH AND WITHOUT VESNARINONE

METHODS FOR INHIBITING CARDIAC FIBROBLAST GROWTH AND CARDIAC FIBROSIS

FIELD OF THE INVENTION

The present invention relates to a method for inhibiting cardiac fibroblast growth, and for inhibiting cardiac fibrosis, wherein said methods use, as the active agent, a carbostyril derivative.

BACKGROUND OF THE INVENTION

I. Carbostyrils

Carbostyril derivatives represented by the following general formula (1), and salts thereof:

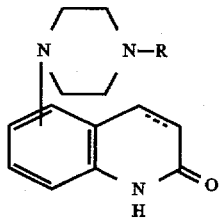

wherein R is a benzoyl group which may optionally have lower alkoxy groups on the phenyl ring as substituents and the carbon-carbon bond in the 3 and 4 positions of the carbostyril skeleton is a single bond or double bond, are well-known in the art (U.S. Pat. No. 4,415,572, which is incorporated by reference herein in its entirety).

These carbostyrils have been found to be an oral inotropic agent that augments myocardial contractility in model systems, with little effect on the heart rate or myocardial oxygen consumption (Feldman et al, *N. Engl. J. Med.*, 329:149–155 (1993)), and are useful for treatment of patients with congestive heart failure (U.S. Pat. No. 4,415,572; and Hori et al, *Jpn. Circ. J.*, 50:659–666 (1986)). Several studies have demonstrated that the above carbostyrils improve hemodynamic indexes, and exercise capacity in congestive heart failure patients (Inoue et al, *Heart Vessels*, 2:166–171 (1986); Sasayama et al, *Heart Vessels*, 2:23–28 (1986); and Feldman et al, *Am. Heart J.*, 116:771–777 (1988)). In addition, multi-center randomized placebo-controlled trials both in Japan and in the United States have demonstrated that these carbostyrils improved quality of life and reduced the risk of death in patients with congestive heart failure (OPC-8212 Multicenter Research Group, *Cardiovasc. Drugs Ther.*, 4:419–425 (1990); Feldman et al, *Am. J. Cardiol.*, 68:1203–1210 (1991); and Feldman et al, *N. Engl. J. Med.*, 329:149–155 (1993)).

The mechanisms of action associated with the inotropic properties of these carbostyrils include a decrease in potassium current (Iijima et al, *J. Pharmacol. Exp. Ther.*, 240:657–662 (1987)), a mild inhibition of phosphodiesterase, and an increase in the inward calcium current (Yatani et al, *J. Cardiovasc. Pharmacol.*, 13:812–819 (1989); and Taira et al, *Arzneimittelforschung*, 34:347–355 (1984)). However, the dose of the carbostyrils which was most effective in reducing mortality (60 mg daily) showed no or little hemodynamic effect, implying that the drug may reduce mortality through another mechanism, rather than its positive inotropic effect (Feldman et al, *N. Engl. J. Med.*, 329:149–155 (1993); and Packer, *N. Engl. J. Med.*, 329:201–202 (1993)).

The above carbostyrils are also known to inhibit the production of various cytokines, including TNF-α and IL-6, by lipopolysaccharide-stimulated peripheral blood mononuclear cells (PBMC) in a dose-dependent manner (Maruyama et al, *Biochem. Biophys. Res. Commu.*, 195:1264–1271 (1993); and Matsumori et al, *Circul.*, 89:955–958 (1994)), and IL-1, thereby inhibiting graft rejection in cardiac implantation (U.S. Pat. No. 5,521,185).

Moreover, they can induce a reversible neutropenia associated with a decrease in CFU-C (Feldman et al, *Am. Heart J.*, 116:771–777 (1988); OPC-8212 Multicenter Research Group, *Cardiovasc. Drugs, Ther.*, 4:419–425 (1990); Feldman et al, *Am. J. Cardiol.*, 68:1203–1210 (1991); and Feldman et al, *N. Engl. J. Med.*, 329:149–155 (1993)).

Additionally, the above carbostyrils have been found to be useful in regulating apoptosis (programmed cell death), and in the treatment of cancer, inhibition of tumor metastasis and inhibition of RNA virus replication (U.S. patent application Ser. No. 07/989,028, filed Apr. 30, 1993, which corresponds to European Patent Publication 0552373, each of which is incorporated by reference herein in their entirety; Nakai et al, *Jpn. J. Cancer Res.*, Abstract, and *Proc. Jpn. Cancer Assoc.*, page 581 (1993); and Maruyama et al, *Biochem. Biophys. Res. Comm.*, 195:1264–1271 (1993)).

The above carbostyrils are also useful for inhibiting DNA virus replication and provide a synergistic effect, when used together with an anti-RNA virus compound, in inhibiting RNA virus replication (U.S. Pat. No. 5,504,093).

Moreover, the above carbostyrils have been found to be useful in inhibiting nucleoside and nucleobase transport, e.g., adenosine, in mammalian cells in a dose-dependent manner, and in augmenting phosphorylation of nucleoside analogues, particularly, AZT (U.S. Pat. No. 5,504,093). Only high concentrations (outside of the therapeutic range) of dipyridamole (10–100 μM), another nucleoside transport inhibitor, inhibit adenosine transport (Scholtissek et al, *Biochem. Biophys. Acta*, 158:435–447 (1968); and Plagemann et al, *J. Membr. Biol.*, 81:255–262 (1984)).

Dipyridamole is proposed to cause a localized increase in adenosine concentration through its inhibition of adenosine transport into cells (Plagemann et al, *Biochem. Biophys. Acta*, 947:405–443 (1988)). Adenosine is known to induce an increase in cAMP in myocardial cells either through activation of adenylate cyclase or through inhibition of phosphodiesterase (Fox et al, *Ann. Rev. Biochem.*, 47:655–686 (1978); and Takeya et al, *Drug Res.*, 34:364–370 (1984)), dilation of coronary arteries (Fox et al, *Ann. Rev. Biochem.*, 47:655–686 (1978)), an increase in cerebral blood flow (Heistad et al, *Am. J. Physiol.*, 240:775–780 (1981)), a decrease in TNF-α production (Parmely et al, *J. Immunol.*, 151:389–396 (1993)), and a decrease in platelet aggregation (Dawicki et al, *Biochem. Pharmacol.*, 34:3965–3972 (1985)), through its binding to specific adenosine receptors on cell surface membranes.

Inhibition of adenosine transport caused by carbostyrils is believed to provide the link with another novel aspect of their action. That is, the above carbostyrils might increase blood concentrations of adenosine by inhibiting adenosine transport, thus explaining some of the therapeutic benefit of vesnarinone in congestive heart disease (Feldman et al, *N. Engl. J. Med.*, 329:149–155 (1993); and Packer, *N. Engl. J. Med.*, 329:201–202 (1993)) or in the reduction of TFN-α production (Maruyama et al, *Biochem. Biophys. Res. Comm.*, 195:1264–1271 (1993); and Matsumori et al, *Circul.*, 89:955–958 (1994)).

Carbostyrils have also been found to give rise to improvements in exercise-induced ischemia without change in heart rate or systolic blood pressure, and to block the progression of ischemia (Kinoshita et al, *Respir. Circ.*, 36:1199–1203 (1988)). Although increases in coronary blood flow may imply attenuation of myocardial ischemia, since the extent of myocardial ischemia is blood flow-dependent, infarct size is not determined by coronary vasodilatory capacity. This is because the coronary artery is completely occluded during myocardial ischemia. The progression of myocardial infarction is attributable to the speed of ATP depletion, and the extent of collateral flow during ischemia, and to platelet and neutrophil activation, $Ca^{+2}$ and catecholamine overload, and oxygen-derived free radical generation. Thus, attenuation of myocardial ischemia due to coronary vasodilation does not necessarily imply limitation of infarct size.

Carbostyrils have also been shown to improve ST depression during exercise in patients with coronary artery disease (Kinoshita et al, supra). The ST-T level in electrocardiogram changes are due to the intra- and extracellular balances in $Ca^{2+}$, $K^+$, $H^+$ and $Na^+$, rotation of the heart, ventricular wall motion, and the presence of ischemia (Noble et al, Cardiovasc. Res., 12:13–17 (1978)). Thus, there is no suggestion therein that carbostyrils can improve myocardial ischemia. Even if myocardial function of the ischemic area is improved due to coronary vasodilation caused by carbostyrils, attenuation of ischemia does not indicate reduction in infarct size. This is because of the multiple coronary blood flow-independent pathogenesis of myocardial necrosis.

The above carbostyrils have recently been found to be useful in reducing infarct size in a subject afflicted with ischemic heart disease (U.S. patent application Ser. No. 08/570,767, filed Dec. 12, 1995).

II. Fibrosis

As discussed above, carbostyrils control apoptosis. Such control has been found in patients with drug-induced hepatitis or viral hepatitis, thereby manifesting a therapeutic effect in hepatitis, and preventing hepatocytes from fibrogenesis (U.S. patent application Ser. No. 07/989,028, filed Apr. 30, 1993, which corresponds to European Patent Publication 0552373). However, such secondary prevention of fibrogenesis, i.e., by destruction of parenchymal cells, is not a viable therapeutic approach for most cardiac diseases. Thus, other effects, directly on fibroblasts, have been sought.

Existing evidence demonstrates the association of fibrosis with the heart failure process in a variety of heart diseases, including those associated with both volume and pressure overload (Maron et al, Am. J. Cardiol., 35:725–739 (1975); Schwarz et al, Am. J. Cardiol., 42:661–669 (1978); Fuster et al, Circ., 55:504–508 (1976); Bartosova et al, J. Physiol., 200:285–295 (1969); Weber et al, Circ., 83:1849–1865 (1991); Schaper et al, Basic Res. Cardiol., 87:S1303–S1309 (1992); Boluyt et al, Circ. Res., 75:23–32 (1994); and Bishop et al, J. Mol. Cell Cardiol., 22:1157–1165 (1990)). In the setting of heart failure, fibrosis involves an increase in both fibroblast number and matrix deposition (Morkin et al, Am. J. Physiol., 215:1409–1413 (1968); Skosey et al, Circ. Res., 31:145–157 (1972); and Booz et al, Cardiovasc. Res., 30:537–543 (1995)), suggesting the importance of the fibroblast in the development of this condition.

Thus, cardiac fibroblasts are the predominant source of synthesis of interstitial proteins and other myocardial components which have been implicated in heart failure by their effects on diastolic function and, indirectly, by effects on cardiac myocytes to cause or potentiate systolic dysfunction (Hess et al, Circ., 63:360–371 (1981); Villari et al, Am J. Cardiol., 69:927–934 (1992); Villari et al, JACC, 22:1477–1484 (1993); Brilla et al, Circ. Res., 69:107–115 (1991); and Sabbah et al, Mol. & Cell Biochem., 147:29–34 (1995)).

Interstitial collagen synthesis is believed to be stimulated by stretch or deformation of fibroblasts (Desrosiers et al, Annales de Chirurgie, 49:768–774 (1995); Sadoshima et al, J. Biol. Chem., 267:10551–10560 (1992); Carver et al, Circ. Res., 69:116–122 (1991); and Butt et al, Ann. N.Y. Acad. Sci., 752:387–393 (1995)) which can be caused by overload states. Though stretch-mediated alteration in ion channel activity has not as yet been demonstrated in fibroblasts, the phenomenon has been observed in other cells (Ruknudin et al et al, Am. J. Physiol., 264:H960–H972 (1993)). The ion channel activities of vesnarinone were postulated in the present invention to modulate the effects of heart disease on fibroblast activity.

In the present invention, it has been unexpectedly discovered that carbostyrils are useful for inhibiting growth of cardiac fibroblasts, and are thus useful for inhibiting cardiac fibrosis.

Although similar in end result to the effects of vesnarinone in preventing hepatic cirrhosis, the effects of vesnarinone on cardiac fibroblasts could not have been predicted from the existing art for the following three reasons:

(1) The mechanism underlying the two responses appear to be quite different and unrelated. Hepatitis leads to fibrosis as a secondary response to hepatocyte necrosis, i.e., vesnarinone appears to prevent fibrosis in this setting by causing non-inflammatory hepatocyte apoptosis instead of inflammation- (and fibrosis-) generating hepatocyte necrosis. In the present invention, the beneficial action of vesnarinone is directly on the fibroblast, not on the parenchymal cells;

(2) The effective dosages for hepatocytes and for cardiac fibroblasts differ significantly: most unexpectedly, the active concentration for cardiac fibroblasts was found in the present invention to be 2.5–25 times lower than that for hepatocytes (i.e., between 4.0 and 40 ng/ml for cardiac fibroblasts vs $\geq 1.0$ μg/ml for hepatocytes); and (3) The hepatocyte's response is directly related to vesnarinone concentration, while cardiac fibroblasts respond in a diametrically opposite fashion, i.e., their response is inversely related to dose; in fact, cardiac fibroblasts are insensitive to the higher doses which affect hepatocytes.

SUMMARY OF THE INVENTION

An object of the present invention is to provide a method for inhibiting growth of cardiac fibroblasts.

Another object of the present invention is to provide a method for inhibiting cardiac fibrosis.

These and other objects of the present invention, which will be apparent from the detailed description of the invention provided hereinafter, have been met by the use of a carbostyril derivative represented by the following general formula (1), and salts thereof:

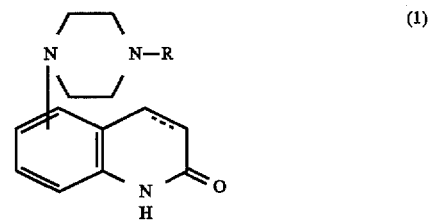

wherein R is a benzoyl group which may optionally have lower alkoxy groups on the phenyl ring as substituents and the carbon-carbon bond in the 3 and 4 positions of the carbostyril skeleton is a single bond or double bond.

BRIEF DESCRIPTION OF THE DRAWINGS

In FIG. 1, each point is the average of all experiments at any one concentration: not all concentrations were tested at the same time or for the same number of times. Data are presented as the ratio of total cell number in a culture treated with vesnarinone (in sulfolane) compared to a matching culture which was not treated with vesnarinone but did contain sulfolane. The 3rd order regression lines are presented for illustrative purposes only since statistical analyses using the Mann-Whitney log ranked test for non-parametric data were performed on the raw data.

DETAILED DESCRIPTION OF THE INVENTION

Figure 1:
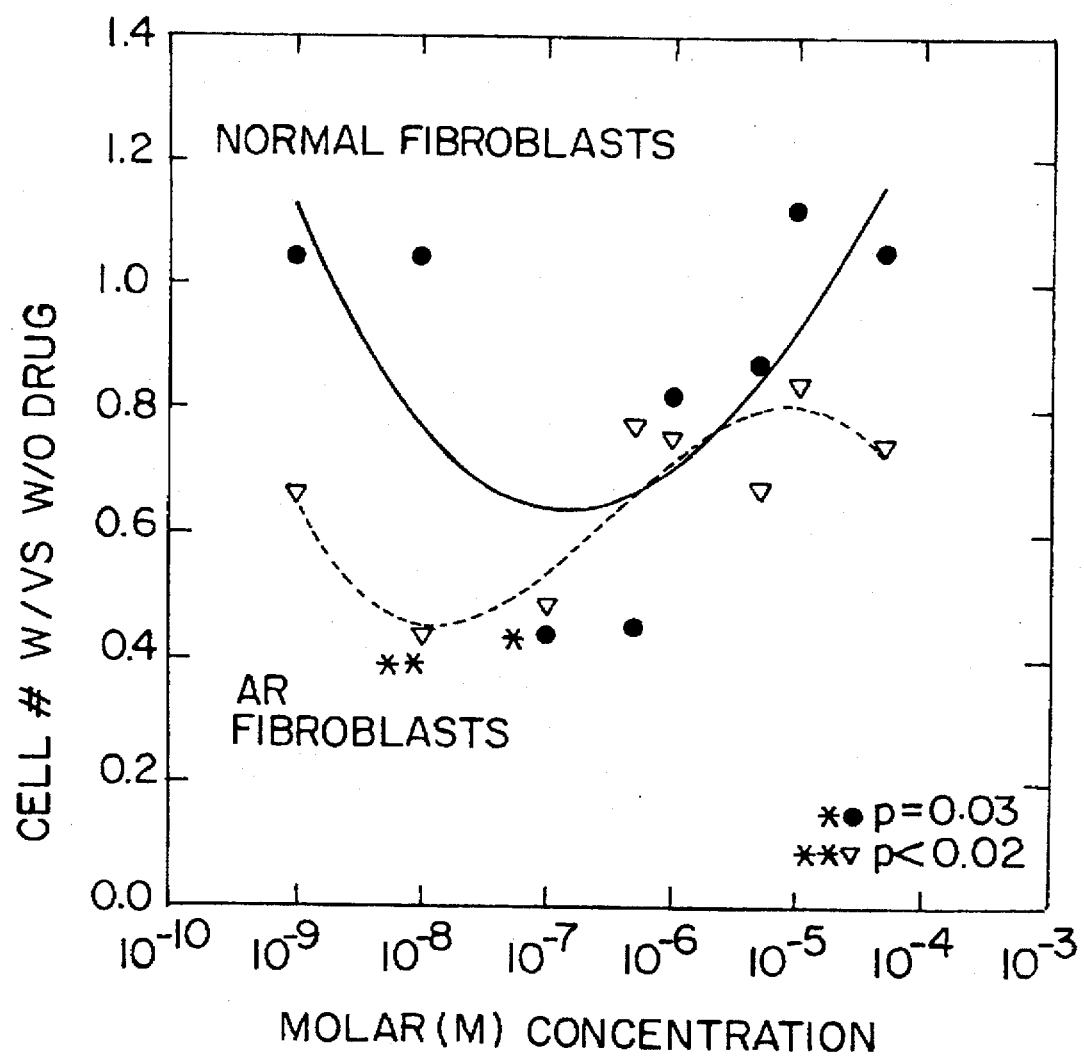
FIG. 1 shows dose response curves for vesnarinone-treated cardiac fibroblasts isolated from normal animals (●), and from animals with chronic aortic regurgitation (v).

As used herein "growth" refers to replication and survival. Thus, the carbostyril derivative represented by formula (1) has been found in the present invention to be useful for inhibiting replication and survival of cardiac fibroblasts.

In general formula (1), the benzoyl group which may have lower alkoxy groups and substituents on the phenyl ring, includes benzoyl groups having 1 to 3 straight-chain or branched $C_{1-6}$ alkoxy groups substituting the phenyl ring, such as benzoyl, 2-methoxybenzoyl, 3-methoxybenzoyl, 4-methoxybenzoyl, 2-ethoxybenzoyl, 3-ethoxybenzoyl, 4-ethoxybenzoyl, 4-isobutoxybenzoyl, 4-hexloxybenzoyl, 3,4-dimethoxybenzoyl, 3,4-diethoxybenzoyl, 3,4,5-trimethoxybenzoyl, 2,5-dimethoxybenzoyl, and so on.

Of the active ingredient compound (1) according to the invention, 3,4-dihydro-6-[4-(3,4-dimethoxybenzoyl)-1-piperazinyl]-2(1H)-quinoline, i.e., vesnarinone, is most preferable.

The above carbostyrils will readily form a salt with a conventional acid. As such acids, there may be mentioned inorganic acids, such as sulfuric acid, nitric acid, hydrochloric acid and hydrobromic acid; and organic acids, such as acetic acid, p-toluenesulfonic acid, ethanesulfonic acid, oxalic acid, maleic acid, fumaric acid, citric acid, succinic acid and benzoic acid. These salts can also be used as the active ingredient in the present invention, just as can the free compound of general formula (1).

In the method for inhibiting growth of cardiac fibroblasts, effective amount will vary depending upon the biological state of the cells prior to treatment, i.e.., normal vs. diseased. Generally, the amount of the compound of formula (1) which is contacted with the cardiac fibroblasts so as to inhibit growth thereof is about $10^{-8}$ to $10^{-7}$ M.

The compounds of general formula (1) and salts thereof, can be generally formulated into the per se conventional pharmaceutical preparations. Such preparations are prepared using conventional fillers, extenders, binding agents, moistening agents, disintegrating agents, surfactants, lubricants, and the like diluents or excipient. These pharmaceutical preparations may have various dosage forms selected according to the purposes of therapy, and typical examples thereof are tablets, pills, powders, solutions, suspensions, emulsions, granules, capsules, suppositories, injections (solutions, suspensions, etc.), and ophthalmic solutions.

For the manufacture of tablets, a wide variety of carriers so far well-known in this field can be used. Thus, use can be made of, for example, vehicles or excipient, such as lactose, sucrose, sodium chloride, glucose, urea, starch, calcium carbonate, kaolin, crystalline cellulose and silicic acid; binding agents, such as water, ethanol, propanol, simple syrup, glucose solution, starch solution, gelatin solution, carboxymethylcellulose, shellac, methylcellulose, potassium phosphate and polyvinylpyrrolidone; disintegrating agents, such as dry starch, sodium alginate, powdered agar, powdered laminaran, sodium hydrogen carbonate, calcium carbonate, polyoxyethylene sorbitan fatty acid esters, sodium lauryl sulfate, stearic acid monoglyceride, starch and lactose; disintegration inhibitors, such as sucrose, stearin, cacao butter and hydrogenated oils; absorption promoters, such as quaternary ammonium bases and sodium lauryl sulfate; wetting agents or humectants, such as glycerol and starch; adsorbents, such as starch, lactose, kaolin, bentonite and colloidal silica; and lubricants, such as refined talc, stearic acid salts, powdered boric acid and polyethylene glycol. When necessary, the tablets may further be provided with a conventional coating to give, for example, sugar-coated tablets, gelatin-coated tablets, enteric-coated tablets, film-coated tablets, or double-coated or multilayer tablets.

For the manufacture of pills, a wide variety of carriers well-known in the art can be used. Examples are vehicles or excipients, such as glucose, lactose, starch, cacao butter, hardened vegetable oils, kaolin and talc; binding agents, such as powdered gum arabic, powdered tragacanth gum, gelatin and ethanol; and disintegrating agents, such as laminaran and agar.

For the manufacture of suppositories, a wide variety of known carriers can be used. As examples, there may be mentioned polyethylene glycol, cacao butter, higher alcohols, higher alcohol esters, gelatin and semisynthetic glycerides.

In preparing injections, the solutions or suspensions are preferably sterilized and are preferably isotonic with blood and, for preparing such dosage forms, all of the diluents in conventional use in the field can be employed. Thus, for example, water, ethyl alcohol, propylene glycol, ethoxylated isostearyl alcohol, polyoxylated isostearyl alcohol and polyoxyethylene sorbitan fatty acid esters may be mentioned. In this case, the pharmaceutical preparations may contain sodium chloride, glucose or glycerol in an amount sufficient to give isotonic solutions. It is possible to add conventional solubilizing agents, buffers, soothing agents or local anesthetics, etc.

Furthermore, when necessary, the pharmaceutical preparations may contain coloring matters, preservatives, perfumes, flavoring agents, sweetening agents and the like, as well as other drugs.

The proportion of the active ingredient compound in these pharmaceutical preparations for use in the present invention is not critical, and may suitably be selected over a wide range. Generally, however, the proportion is recommendably selected within the range of about 1.0 to about 70% by weight, preferably about 1.0 to about 30% by weight.

The route of administration of the pharmaceutical preparations of the present invention is not critical, either, but is selected according to the dosage form, the patient's age, sex and other factors, and the severity of the cardiac fibrosis to be treated. Thus, for instance, when they are provided in the form of tablets, pills, solutions, suspensions, emulsions, granules or capsules, the preparations are administered orally. Injectable solutions are administered intravenously, either alone or in admixture with conventional fluids for parental infusion containing glucose, amino acids and so on. Where necessary, these solutions may also be administered as is by the intramuscular, intradermal, subcutaneous or intraperitoneal route. Suppositories are administered rectally, ophthalmic solutions are drop lotions for the eyes.

While the dosage of the above pharmaceutical preparations is dependent on the method of administration, the patient's age, sex and other background factors, severity of the disease and the disease to be treated, it is generally recommended to administer orally about 5 to 60 mg/per day, or the equivalent intravenous dose based upon plasma levels.

Cardiac fibrosis in the present invention may be due to a variety of diseases associated with cardiac fibroblast proliferation or the activation of extracellular matrix protein synthesis by cardiac fibroblasts. These diseases may be effectively treated in the present invention. Such diseases include aortic and mitral valvular regurgitation. In addition, cardiac hypertrophy, which is associated with many cardiac diseases, and often involves myocyte and fibroblast components, may be effectively treated in the present invention.

| Dosage Form Example 1 | |
|---|---|
| 3,4-dihydro-6-[4-(3,4-dimethoxybenzoyl)-1-piperazinyl]-2(1H)-quinoline | 150 g |
| Avicel | 40 g |
| (trademark, Asahi Chemical Industry, Co., Ltd.) | |
| Corn starch | 30 g |
| Magnesium stearate | 2 g |
| Hydroxypropylmethylcellulose | 10 g |
| Polyethylene glycol 6000 | 3 g |
| Castor oil | 40 g |
| Methanol | 40 g |

The above active ingredient, Avicel, corn starch and magnesium stearate are mixed and ground together, and the resulting mixture is compression-molded with a dragee R10 mm punch. The tablets thus obtained are coated with a film coating composition consisting of hydroxypropyl methylcellulose, polyethylene glycol 6000, castor oil and methanol to give film-coated tablets.

| Dosage Form Example 2 | |
|---|---|
| 3,4-dihydro-6-[4-(3,4-dimethoxybenzoyl)-1-piperazinyl]-2(1H)-quinoline | 150 g |
| Citric acid | 1 g |
| Lactose | 33.5 g |
| Dicalcium phosphate | 70 g |
| Pluronic F-68 | 30 g |
| Sodium lauryl sulfate | 15 g |
| Polyvinylpyrrolidone | 15 g |
| Polyethylene glycol (Carbowax 1500) | 4.5 g |
| Polyethylene glycol (Carbowax 6000) | 45 g |
| Corn starch | 30 g |
| Dry sodium lauryl sulfate | 3 g |
| Dry magnesium stearate | 3 g |
| Ethanol | q.s. |

The above active ingredient, citric acid, lactose, dicalcium phosphate, pluronic F-68 and sodium lauryl sulfate are admixed.

After size selection using a No. 60 screen, the mixture is granulated by the wet process using an alcoholic solution containing polyvinylpyrrolidone, Carbowax 1500 and Carbowax 6000. When necessary, alcohol is added to make the powder into a paste-like mass. Then, corn starch is added, and the blending is continued until uniform granules are formed. The mixture is then passed through a No. 10 screen, placed in a tray and dried in an oven maintained at 100° C. for 12 to 14 hrs. The dried granules are sieved through a No. 16 screen, then dry sodium lauryl sulfate and dry magnesium stearate are added and, after blending, the mixture is compressed to a desired size and shape using a tableting machine.

The above cores are treated with a varnish and dusted with talc for preventing absorption of moisture, and then provided with an undercoat layer. Varnish coating is repeated as many times as sufficient for internal use. The tablets are rendered completely round and smooth by application of a further undercoat layer and a smooth coating. Color coating is conducted until a desired coloring is obtained. After drying, the coated tablets are polished to give uniformly polished tablets.

The following example is provided for illustrative purposes only, and is in no way intended to limit the scope of the present invention.

EXAMPLE

Tissue culture is well-established as a model system for heart disease (Douglas et al, In: Research Animals and Concepts of Applicability to Clinical Medicine, Eds. Gartner et al, S. Karger, Basel, pp. 196–204 (1982); Zoller et al, J. Molec. Cell. Cardiol., 26:627–638 (1994); and Ni et al, Cell. Biol. Toxicol., 8:1–11 (1992)), and tissue culture cells (particularly fibroblasts), are used to determine toxicity, dose response curves and mechanisms of action in pharmacologic studies. The rabbit also is well-established as a model system for cardiovascular disease (Gardner et al, In: Experimental Surgery and Physiology: Induced Animal Models of Human Disease, Eds. Swindle et al, Williams and Wilkins, Baltimore, pp. 74–113 (1988); Fizelova et al, Res. Adv. Stud. Cardiol. Struc. Metab., 1:200–210 (1972); Young et al, Am. J. Noninvasive Cardiol., 4:145–153 (1990); and Magid et al, Am. J. Physiol., 263:H226–H233 (1992)).

A. Cell Isolation

A total of 7 cell isolations were performed, leading to the establishment of 6 primary cardiac fibroblast cell lines. Two of these lines were obtained from normal New Zealand White rabbits (average age—27 weeks), 1 was from a sham-operated rabbit (age—225 weeks; 201 week post-operation) and 3 were from rabbits with surgically induced aortic regurgitation (AR) (average age—110 weeks; 93 weeks post-operation).

Cells were isolated using a collagenase perfusion procedure similar to those described by Mitra et al, Am. J. Physiol., 249:H1057–H1060 (1985) and Tytgat, Cardiovas. Res., 28:280–283 (1994), and were grown in complete culture medium comprising Minimal Essential Medium containing 5.0% (v/v) fetal bovine serum, 5.0% (v/v) Nu-Serum (Collaborative Biomedical Products, Becton Dickinson, Bedford, Mass.), with antibiotics/antimycotics (100 units/ml penicillin G, 100 units/ml streptomycin and 0.25 units/ml amphotericin B (GIBCO BRL, Gaithersburg, Md.)), for up to 8 passages.

The cells were immunologically characterized as fibroblasts by indirect immunofluorescence microscopy using antibodies against vimentin, desmin, smooth muscle α-actin and smooth muscle myosin, as described by Eghbali et al, J. Mol. Cell Cardiol., 20:267–276 (1988).

B. Dose Response Curve

To determine an effective concentration of vesnarinone for use in all subsequent experiments, a dose-response curve was constructed. More specifically, concentrations from $1.0 \times 10^{-4}$ M to $1.0 \times 10^{-6}$ M of vesnarinone, were first evaluated. Thereafter, the dose range was expanded downward to include concentrations as low as $1.0 \times 10^{-9}$ M vesnarinone.

In 12 experiments, using fibroblasts cultured from normal hearts (n=2 hearts), and 7 experiments using fibroblasts cultured from AR hearts (n=2 hearts), a total of $1.0 \times 10^5$ cells were plated in T25 culture flasks and grown overnight in complete culture medium described above at 37° C. Vesnarinone was then added in the various concentrations to be evaluated. In all of these experiments, sulfolane was used as a vehicle to solubilize the vesnarinone. Therefore, all of the cultures were adjusted to give a constant concentration (0.33% (v/v)) of sulfolane and sulfolane, alone, was used as a negative control for all comparisons. The cultures were harvested by trypsinization after a second overnight incubation at 37° C. Total cell numbers were determined by counting using Trypan Blue. Samples were frozen for total DNA and protein analyses. The results are shown in FIG. 1.

As shown in FIG. 1, at $1.0-5.0 \times 10^{-7}$ M vesnarinone, normal fibroblast cell number was about 55% less than in the sulfolane-alone control (p=0.03). At higher concentrations, the cell number gradually increased, peaking slightly above control at $1.0 \times 10^{-5}$ M vesnarinone. A comparable, statistically significant (p<0.02) reduction in cell number also was seen in the AR cultures when relatively low concentrations of vesnarinone were applied. However, this effect was observed at $1.0 \times 10^{-8}$ M vesnarinone, a concentration an order of magnitude lower than the lowest effective concentration for normal cells. Also, in AR studies, the cell number never reached or exceeded sulfolane-alone control at any of the drug concentrations tested.

These results are believed to be attributable to a differential response by fibroblasts from normal and AR hearts. The differences between cultures treated with a low concentration of vesnarinone and those treated with no vesnarinone at all were statistically significant both for normal and AR studies, and a dose-response relation was apparent. The presence of a significant dose response relation indicates that the effect of the drug is not likely to have resulted from chance alone. Importantly, the plasma concentration of vesnarinone in humans taking 60 mg/day orally is approximately $1.7 \times 10^{-5}$ M; accounting for likely differences in circulating plasma concentrations and in tissue concentrations. Thus, the results indicate that fibroblast viability may be affected by vesnarinone concentrations comparable to those present in the myocardium at therapeutic oral doses.

C. Chronic Exposure

Next, experiments were performed using fibroblasts isolated from 3 animals (2 normal, 1 AR). In these experiments, parallel cultures containing a total of $1.0 \times 10^5$ cells plated in complete medium either with or without $1.0 \times 10^{-6}$ M sulfolane-solubilized vesnarinone were allowed to grow for up to 14 days at 37° C. One vesnarinone and one control culture were harvested each day by trypsinization and counted to determine the number of viable cells per culture. The results are shown in FIG. 2.

Figure 2:
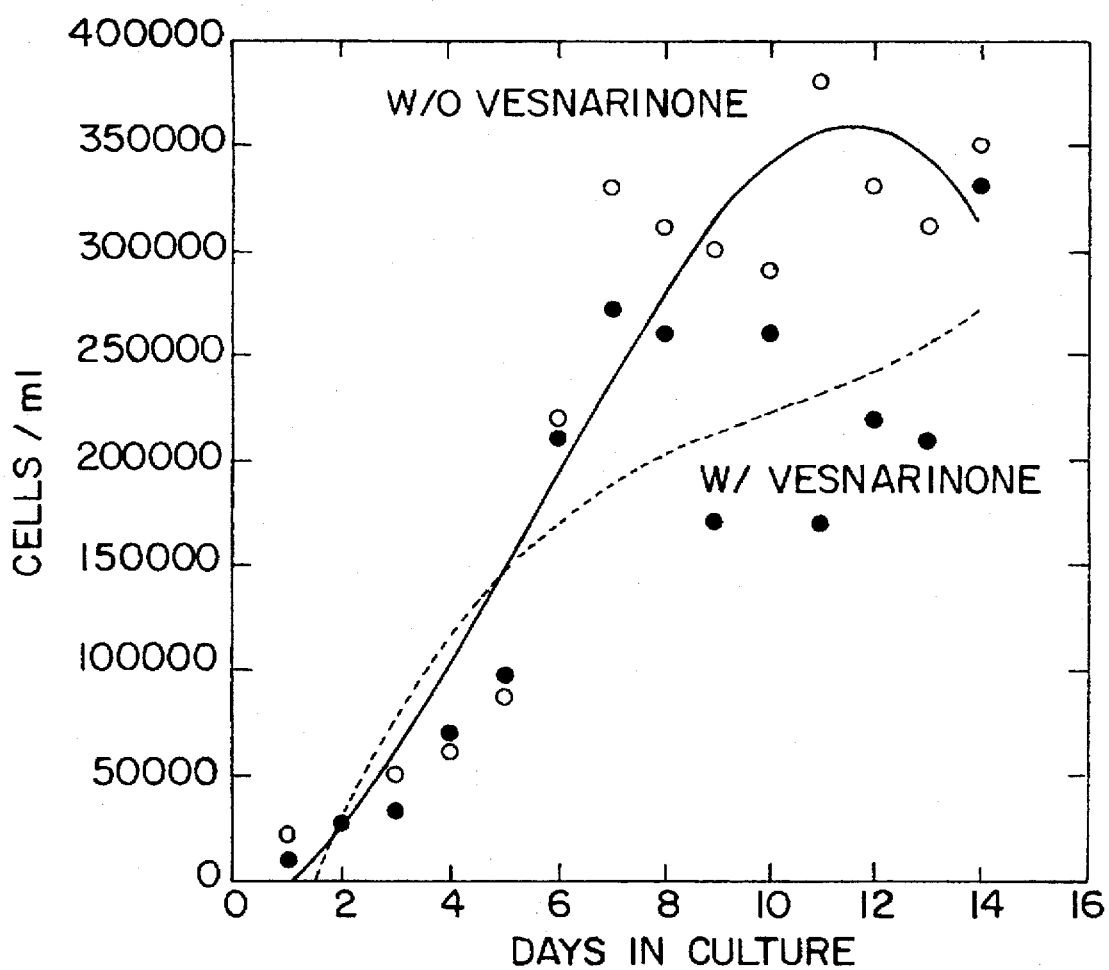
FIG. 2 shows the effects on normal cardiac viability over time when exposed to $10^{-6}$ M vesnarinone (●). Unexposed normal cardiac viability over time is also shown (o). The illustrative regression lines were constructed using a standard curve-fitting algorithm.

As shown in FIG. 2, chronic exposure to a vesnarinone concentration higher than that which causes reduction in cell number also affects cardiac fibroblast viability over time. During the period of observation (up to 14 days), in normal cell cultures, the number of cells in the $10^{-6}$ M vesnarinone-treated cultures decreased compared to those exposed to sulfolane alone. In this experiment, cultures with or without vesnarinone contained similar numbers of cells up to day 6. After that time, the number of cells in the vesnarinone treated cultures declined relative to the control, untreated, cultures. Similar results were observed in the experiment performed with AR cells. This result could not be due to the accumulation of toxic break-down products since, in all cases the culture medium was changed every 3rd or 4th day.

D. Cell Morphology

Cellular morphology also was examined using phase contrast microscopy. Observations were made on cells in both the dose response and chronic exposure studies.

No noteworthy effect on morphology was seen at any concentration tested.

E. Apoptosis Effect

Several processes might account for the reduction in cell numbers seen in cultures treated acutely with nanomolar vesnarinone concentrations, or in cultures treated chronically with micromolar vesnarinone concentrations. One possible explanation for the findings is that vesnarinone is toxic to cardiac fibroblasts. If this explanation were correct, vesnarinone might either kill cells outright or might induce apoptosis (programmed cell death). Because cell number exhibited a bimodal response to vesnarinone, with greater survival at higher doses, evidence of apoptosis at low doses was sought, reasoning that this effect might be overcome at higher doses while direct toxicity would be less likely to respond to dose in this way.

Apoptosis was tested for in confluent cultures containing more than $1.0 \times 10^6$ cells. These cultures were treated overnight with $5.0 \times 10^{-7}$ M vesnarinone, harvested by trypsinization, fixed in formalin and then were stained for evidence of stereotyped DNA fragmentation (a marker for apoptosis) using a commercially available in situ terminal deoxynucleotidyl transferase labeling kit (Oncor, Apoptag-Plus). In this assay, viable cells appear red while those cells undergoing apoptosis appear a yellow-green color.

The initial experiments on normal fibroblasts (3 experiments) revealed that cultures treated with vesnarinone have nearly twice the number of apoptotic cells as do untreated cultures (6.1% vs. 3.4%; $p \leq 0.1$; n=3).

F. Summary

The results indicate that vesnarinone reduces viability of normal cardiac fibroblasts at concentrations comparable to those achieved with currently conceived therapeutic oral doses in man and at concentrations lower than those shown by others to affect lung carcinoma cell growth in culture. The results indicate that this effect is even more prominent in cardiac fibroblasts isolated from hearts exposed chronically to the severe volume loading of AR. The experiments also indicate that this phenomenon is observable when higher doses are used chronically. The effect of vesnarinone on fibroblasts appear to be mediated, at least in part, by induction of apoptosis.

The results indicating that fibroblast viability is not affected acutely by relatively high vesnarinone concentrations ($\geq 10^{-6}$ M) are consistent with those on various non-cardiac fibroblasts in culture (Yoshinaka et al, *Exp. Cell Res.*, 219:21–28 (1995)). However, in contrast to those studies, vesnarinone-induced morphological alterations of cardiac fibroblasts using phase contrast microscopy were not observed. Alterations to cellular stress fibers should be detectible with this form of microscopy.

While the invention has been described in detail, and with reference to specific embodiments thereof, it will be apparent to one of ordinary skill in the art that various changes and modifications can be made therein without departing from the spirit and scope thereof.

What is claimed:

1. A method for inhibiting cardiac fibroblast growth comprising contacting cardiac fibroblasts with an effective amount of a carbostyril derivative represented by the following general formula (1), or a pharmaceutically acceptable salt thereof:

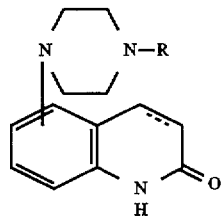

wherein R is a benzoyl group which may optionally have lower alkoxygroups on the phenyl ring as substituents and the carbon-carbon bond in the 3 and 4 positions of the carbostyril skeleton is a single bond or double bond.

2. The method of claim 1, wherein said carbostyril is 3,4-dihydro-6-[4-(3,4-dimethoxybenzoyl)-1-piperazinyl]-2 (1H)-quinoline or a pharmaceutically acceptable salt thereof.

3. A method for inhibiting cardiac fibrosis in a subject in need of such treatment, comprising administering to said subject a pharmaceutically effective amount of a carbostyril derivative represented by the following general formula (1), or a pharmaceutically acceptable salt thereof:

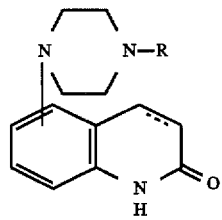

wherein R is a benzoyl group which may optionally have lower alkoxy groups on the phenyl ring as substituents and the carbon-carbon bond in the 3 and 4 positions of the carbostyril skeleton is a single bond or double bond.

4. The method of claim 3, wherein said carbostyril is 3,4-dihydro-6-[4-(3,4-dimethoxybenzoyl)-1-piperazinyl]-2 (1H)-quinoline or a pharmaceutically acceptable salt thereof.

5. The method of claim 3, wherein said cardiac fibrosis in said subject is due to a cardiac disease selected from the group consisting of aortic valvular regurgitation and mitral valvular regurgitation.

* * * * *